United States Patent
Rosen

(10) Patent No.: US 6,821,121 B2
(45) Date of Patent: Nov. 23, 2004

(54) CONSUMER USABLE CHIPPED AND/OR FRACTURED TOOTH DENTAL INSTRUMENT

(76) Inventor: Gregory J. Rosen, 3 S. Elberon Sq., Long Branch, NJ (US) 07740

( * ) Notice: Subject to any disclaimer, the term of this patent is extended or adjusted under 35 U.S.C. 154(b) by 104 days.

(21) Appl. No.: 10/224,266

(22) Filed: Aug. 21, 2002

(65) Prior Publication Data

US 2004/0038177 A1 Feb. 26, 2004

(51) Int. Cl.⁷ .................................................. A61C 3/06
(52) U.S. Cl. ...................................................... 433/142
(58) Field of Search ................................ 433/102, 141, 433/142, 143, 144, 145, 146, 147, 165, 166; 206/369; 15/236.07; 132/76.4

(56) References Cited

U.S. PATENT DOCUMENTS

| | | | | |
|---|---|---|---|---|
| 273,821 A | * | 3/1883 | Crosthwaite | 433/144 |
| 3,504,440 A | * | 4/1970 | Fontana | |
| 4,060,897 A | * | 12/1977 | Greenstein | |
| 4,274,826 A | * | 6/1981 | Huey et al. | 433/144 |
| 4,377,381 A | * | 3/1983 | Westman | 433/141 |
| 4,559,957 A | * | 12/1985 | Hokama | 132/73 |
| 4,642,894 A | * | 2/1987 | Campbell | 433/143 |
| 4,690,642 A | * | 9/1987 | Kyotani | 433/142 |
| 4,781,590 A | * | 11/1988 | Weinstein | 433/142 |
| 6,217,330 B1 | * | 4/2001 | Danger | 433/166 |
| 6,397,860 B1 | * | 6/2002 | Hill, II | 132/309 |
| 6,533,580 B1 | * | 3/2003 | Mondi | 433/142 |

* cited by examiner

*Primary Examiner*—Cary E. O'Connor
(74) *Attorney, Agent, or Firm*—Charles I. Brodsky

(57) ABSTRACT

A dental instrument consisting of a handle having first and second opposing ends, and a metal bur at at least one of the ends, which includes a diamond-chip coating, and of given shape and angulation, exhibiting a hardness characteristic sufficient to smooth dental enamel when filed thereacross, with the instrument included within a blister pack for consumer purchase as an emergency treatment relief device.

1 Claim, 2 Drawing Sheets

CONSUMER USABLE CHIPPED AND/OR FRACTURED TOOTH DENTAL INSTRUMENT

CROSS-REFERENCE TO RELATED APPLICATIONS

None

STATEMENT REGARDING FEDERALLY SPONSORED RESEARCH OR DEVELOPMENT

Research and development of this invention and Application have not been federally sponsored, and no rights are given under any Federal program.

REFERENCE TO A MICROFICHE APPENDIX

Not Applicable

BACKGROUND OF THE INVENTION

1. Field of the Invention

This invention relates to the treatment of chipped and/or fractured dental teeth, in general, and to an emergency treatment device for providing at least temporary relief in avoiding possible injurious effects therefrom, in particular.

2. Description of the Related Art

As is well known and understood, studies document that over 50% of the population do not ever treat with a dentist on a regular basis. Studies also shown that even in dental emergencies, large portions of the populace do not seek professional assistance, but attempt to deal with the problem themselves. Even for those who have regular dental appointments, or seek help when a problem arises, many are the times when seeing a dentist, even on an emergency basis, is not feasible. For such instances,pharmacies oftentimes stock items for emergency treatment by the consumer on an individual basis—until such time as a visit to a dentist could be scheduled. Typical of these are the widely available types of remedies to ease and/or deaden the effects of toothache pain.

While such topical pain killers are generally effective, problems often continue where the cause of the discomfort is a chipped and/or fractured tooth. Whereas most dentists regard such situations as ones requiring emergent treatment, many times an availability of the dentist to see a patient just cannot be arranged. Besides the continuing discomfort the patient suffers while waiting to return from a vacation, for example, or if occurring late at night (especially on a weekend), when first seeing the dentist, the chipped and/or fractured tooth can lead to other problems—such as lacerations of the cheek, lacerations of the tongue, and canker sores. Investigation and analysis of the situation reveals that there generally is nothing available on the market to assist the distressed person in these circumstances—short of finding a dentist to treat the tooth insult.

SUMMARY OF THE INVENTION

As will become clear from the following description, the present invention recognizes the desirability of having a dental instrument, simple enough for a consumer to employ himself/herself, and available for purchase in a pharmacy to deal with the chipped and/or fractured tooth until such time as a dentist can be visited. As will also be seen, the unique dental instrument of the invention follows the recognition that dental enamel is essentially the hardest bone in the body and, therefore, requires an instrument of even greater hardness. As will be understood from the description that follows, such a consumer usable dental instrument intended for pharmacy availability includes a handle having first and second opposing ends, along with a metal bur at at least one of the ends including a diamond-chip coating; and of given shape and angulation to fit within the mouth in smoothing the dental enamel of the affected tooth, wherever it may be positioned. In a preferred embodiment, the metal bur along with its diamond-chip coating is secured with a plastic handle at each of its opposing ends, and exhibits a hardness characteristic sufficient to smooth the dental enamel when being filed across it. In one such construction, with a diamond-ship coating of fine grain, the metal bur may be fused to the plastic handle in manufacture, or may alternatively include a shank to be fitted within the handle end—the diamond-chip coated smoothing surface being then located at the remote end of the shank. When included within a blister pack for sale, the dental instrument of the invention becomes readily purchasable from a pharmacy as an emergency treatment device to smooth the damaged tooth, in providing temporary relief until the dentist can be seen.

As will be appreciated, a diamond-chip coating of fine grain offers the advantage of allowing an enamel filing without skipping over the myriad of its surfaces, while employing different shapes and/or angulation to the bur enables the most efficient smoothing in the mouth wherever the chipped and/or fractured tooth might be.

BRIEF DESCRIPTION OF THE DRAWINGS

These and other features of the present invention will be more clearly understood from a consideration of the following description, taken in connection with the accompanying drawings, in which.

DETAILED DESCRIPTION OF THE INVENTION

Figure 1:
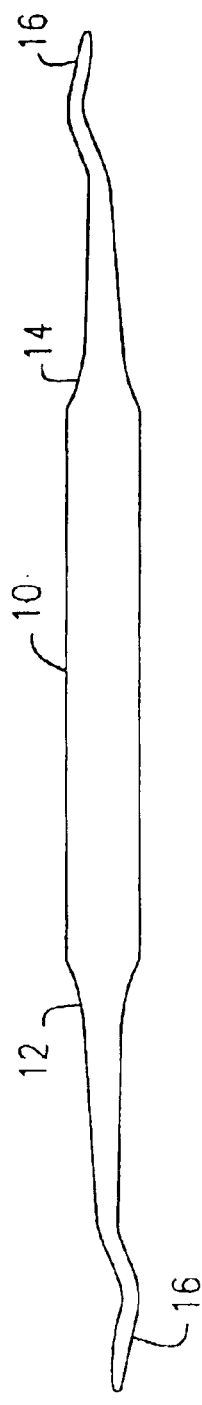
FIG. 1 is a front view of the,consumer usable chipped and/or fractured tooth dental instrument constructed in accordance with the teachings of the invention, with a rear view thereof being substantially a mirror image, but with a different grain of abrasive.

Referring to the drawings, the consumer usable chipped and/or fractured tooth dental instrument of the invention comprises a handle 10, preferably of plastic, having first and second opposing ends 12, 14. A metal bur 16, in accordance with the invention, may be secured with one of the two ends, or fabricated there as part of the plastic handle itself—although in the preferred embodiment of the drawings, a pair of metal burs 16 are included, one at each of the opposing ends 12, 14. Such bur(s) 16 includes a diamond-chip coating 18 (also, preferably of fine grain), and of given shape and angulation so as to fit within a user's mouth on either the inside or outside of the gingiva in forming a dental instrument. As illustrated in the various drawings, the two burs 16 are each of differing angles, though with each being provided with the coating 18 on a generally planar surface 20.

The diamond-chip coating is selected to exhibit a hardness characteristic sufficient to smooth the dental enamel of a chipped and/or fractured tooth when filed across it.

Figure 2:
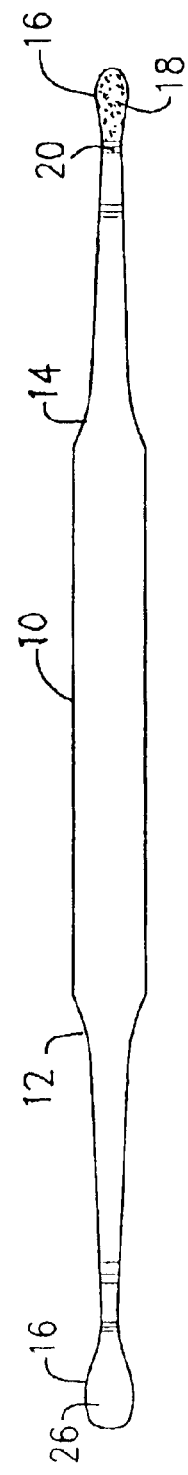
FIG. 2 is a top view of the dental instrument of FIG. 1.
Figure 3:
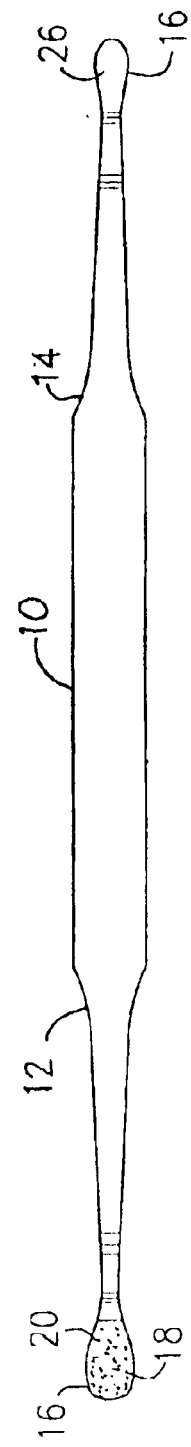
FIG. 3 is a bottom view helpful in an understanding of the invention.
Figure 4A:
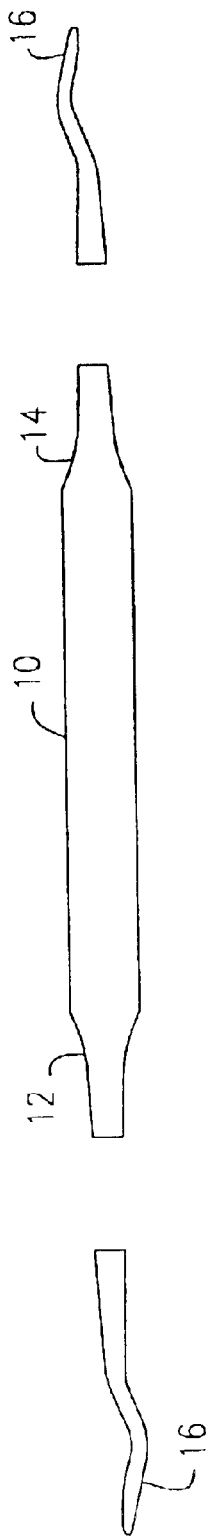
FIGS. 4A and 4B are disassembled views of the dental instrument of FIG. 1 helpful in an understanding of alternative constructions for its use.
Figure 4B:
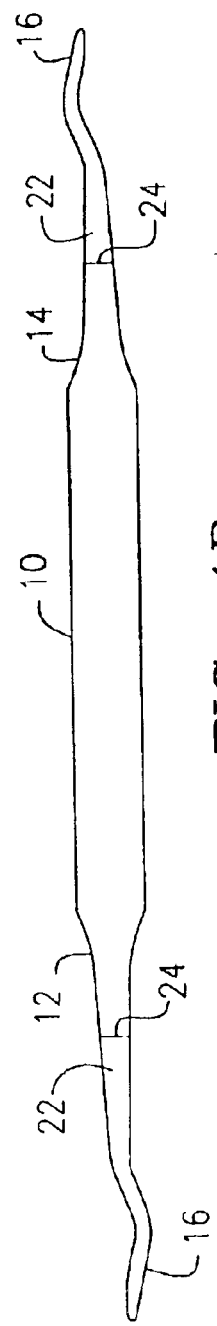

In the construction of FIGS. 1–3, the metal bur(s) 16 are illustrated as being of a type fused to the plastic handle 10 in construction; such configuration is dis-assembled in FIG. 4A, while with the alternative construction of FIG. 4B, the bur(s) 16 may be located at the remote end of a shank 22 configured to fit within a receiving end 24 of the handle 10 by any "male-female" join.

As illustrated in FIGS. 1–3, the two burs 16 are aligned at differing angles, with a diamond-chip coating 18 provided about their opposing planar surfaces 20. As will be appreciated, however, such coatings 18 could be incorporated, if desired, on both the top and the bottom surfaces at the bur ends—20 and 26—to allow for the smoothing of any chip and/or dental fracture by the user, without his/her having to resort to visiting a dentist to accomplish the smoothing task.

By having the handle fabricated of "plastic", with the metal bur 16 and its diamond-chip coating 18 only at one end, a consumer usable dental instrument of this type could be fabricated for purchase as an emergency dental treatment relief device for a nominal cost; adding a coating at the opposite end, and/or on top and bottom planar surfaces increases the cost only a moderate amount. Included within a blister pack for such sale, the dental instrument could be obtainable as an emergency treatment relief device from a pharmacy. In the event that a tooth becomes chipped or fractured, the dental instrument of the invention could be used by easy manipulation to smooth the dental enamel. An expensive visit to a dentist could thus be avoided—or at least temporarily put off until one could be conveniently seen. Employing different shapes and angulations in this manner allows for an efficient smoothing of the problem wherever the chipped and/or fractured tooth might be.

Figure 5:
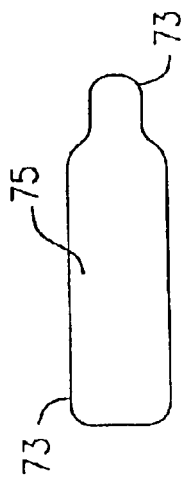
FIG. 5 is a top view helpful in understanding an alternative embodiment of the invention.

While there have been described what are considered to be preferred embodiments of the present invention, it will be readily appreciated by those skilled in the art that modifications can be made without departing from the scope of the teachings herein. For example, whereas particular shapes and angulations have been shown for the surfaces 20 or 26 of the drawings, other designs and configurations could be employed, as could the use of a variety of metal or metal surface burs, in supporting the diamond-chip coating (or other comparable abrasive) of the invention; one such particularly attractive bur design may resemble a shape comparable to that of the silhouette of a bottle, having round line angles to avoid inadvertently lacerating the gingiva/soft tissue when in use, and a metal thickness to resist bending or breakage (FIG. 5, the round line angles being shown at 73 for the bottle shape 75). And, whereas diamond-chip coatings of fine grain are preferable, others of medium and even coarse grain might be employable although far less effective in providing a smoothing action upon the damaged enamel. Also, and as will be appreciated, such burs could be attached as an abrasive diamond-chip coated disc instead, to a battery powered electric toothbrush to provide the tooth smoothing action desired. For at least such reason, therefore, resort should be had to the claims appended hereto for a true understanding of the scope of the invention.

I claim:

1. A consumer usable chipped and/or fractured tooth dental instrument, comprising:

a handle having a graspable first end of given cross-section dimension and a second opposing end of abrasive material exhibits a hardness characteristic sufficient to smooth dental enamel when filed thereacross;

with said handle being of round curvature at said second end, with a cross-section dimension thereat less than that of said first end;

wherein said second end of said handle contains a diamond-chip coating thereon;

wherein said handle is fabricated of a metal composition of a thickness to resist bending or breakage in use; and wherein said handle is of substantially flat, bottle-shaped configuration.

* * * * *